United States Patent
Ramzipoor

(12)
(10) Patent No.: US 6,254,549 B1
(45) Date of Patent: Jul. 3, 2001

(54) GUIDEWIRE REPLACEMENT DEVICE WITH FLEXIBLE INTERMEDIATE SECTION

(75) Inventor: Kamal Ramzipoor, Union City, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/285,808

(22) Filed: Apr. 1, 1999

Related U.S. Application Data

(63) Continuation of application No. 08/616,449, filed on Mar. 15, 1996, now Pat. No. 5,891,056.

(51) Int. Cl.$^7$ ........................................... A61B 5/00
(52) U.S. Cl. ........................................................ 600/585
(58) Field of Search ................................. 600/433, 434, 600/585; 604/95, 96, 280

(56) References Cited

U.S. PATENT DOCUMENTS

| | | | |
|---|---|---|---|
| 5,391,146 | * 2/1995 | That et al. | 604/95 |
| 5,415,639 | 5/1995 | VandenEinde et al. | 604/283 |
| 5,437,288 | 8/1995 | Schwartz et al. | 128/772 |
| 5,449,362 | * 9/1995 | Chaisson et al. | 606/108 |
| 5,540,236 | * 7/1996 | Ginn | 600128/585 |

FOREIGN PATENT DOCUMENTS

WO 93/13827   7/1993   (WO).
WO 96/04035   2/1996   (WO).

* cited by examiner

*Primary Examiner*—John P. Lacyk
*Assistant Examiner*—Pamela L. Wingood
(74) *Attorney, Agent, or Firm*—Heller Ehrman White & McAuliffe LLP

(57) ABSTRACT

A guidewire replacement device having a proximal shaft section, a distal shaft section and a flexible intermediate shaft section which facilitate the articulation of the distal shaft section with respect to the proximal shaft section. The intermediate shaft section has as aperture for the egress or exit of an in-place guidewire during a guidewire exchange. The proximal end of an in-place guidewire is inserted through the distal guidewire port in the distal end of the distal shaft section, through the distal section and out the aperture in the intermediate shaft section. The exchange device is advanced through the inner lumen of a guiding catheter over the in-place guidewire until the distal end of the exchange device extends through the proximal guidewire port of a rapid exchange type intraluminal catheter. Once the guidewire exchange device is properly placed, the in-place guidewire can then be withdrawn from the patient. The replacement guidewire can then be advanced through the inner lumen of the proximal shaft section, the guidewire passageway of the intermediate section, the inner lumen of the distal section into the guidewire receiving inner lumen of the intraluminal catheter. The guidewire exchange device may then be removed from the patient.

7 Claims, 3 Drawing Sheets

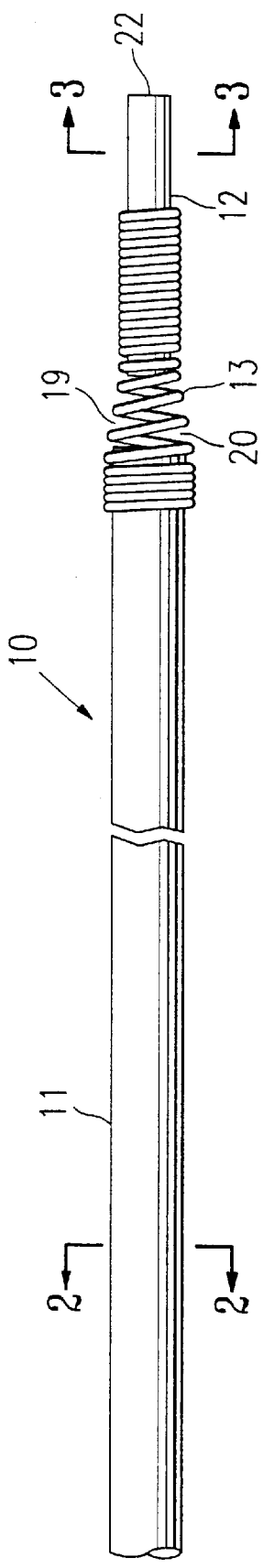
FIG. 1
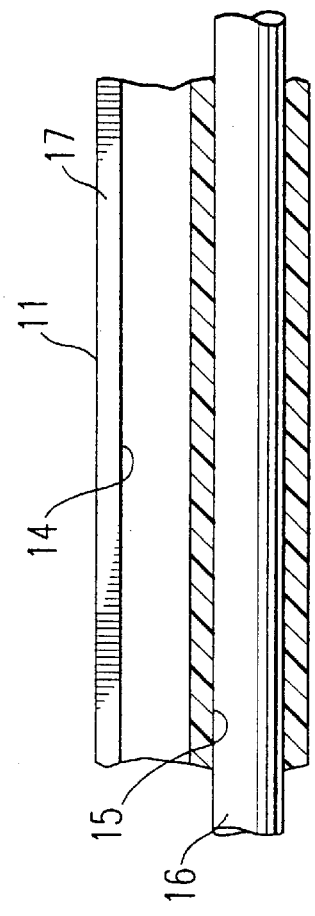
FIG. 4
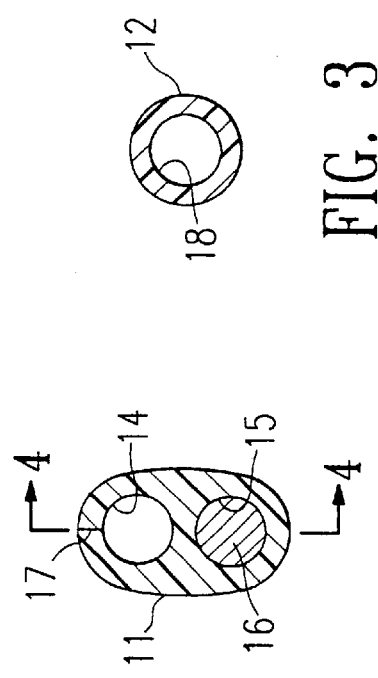
FIG. 3
FIG. 2

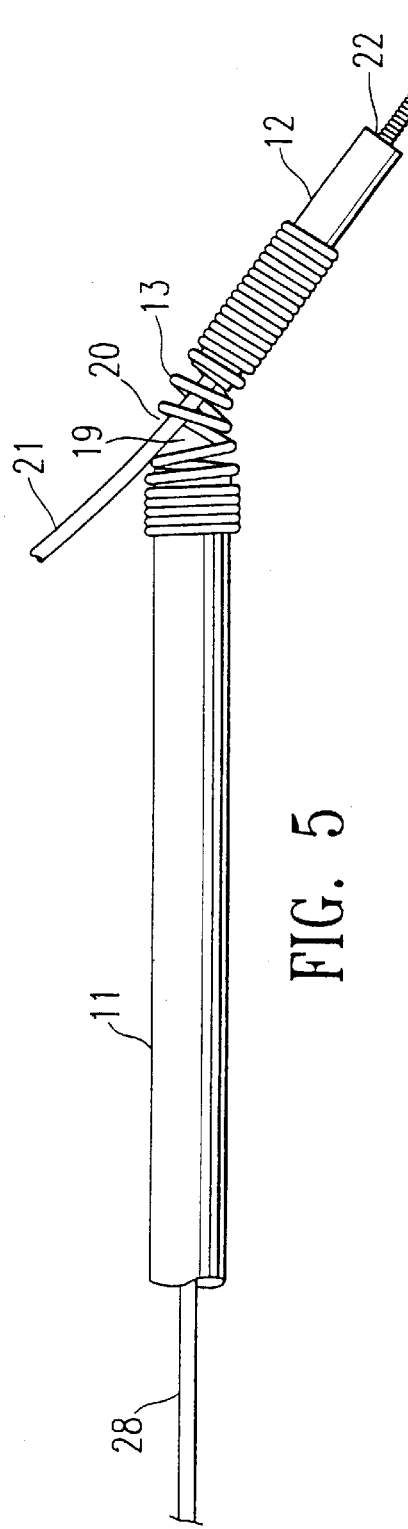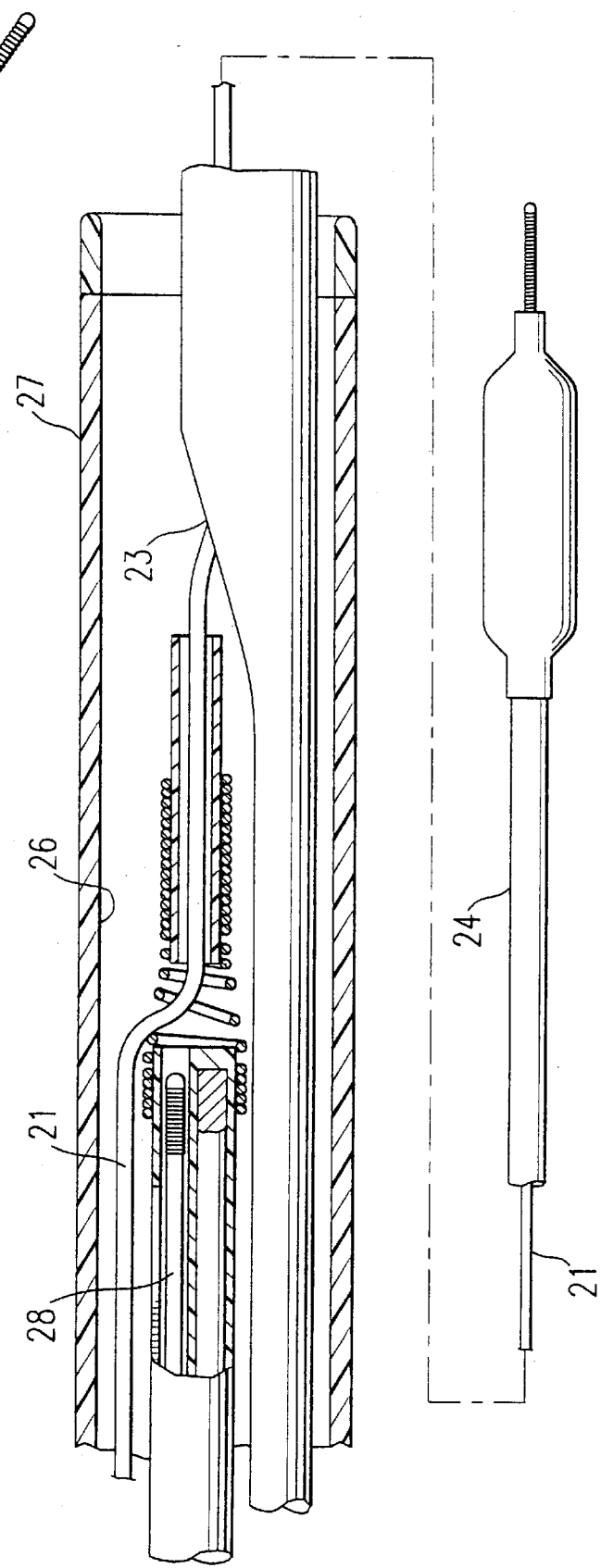

GUIDEWIRE REPLACEMENT DEVICE WITH FLEXIBLE INTERMEDIATE SECTION

This is a continuation of application Ser. No. 08/616,449 filed Mar. 15, 1996 now U.S. Pat. No. 5,891,056, incorporated by reference.

BACKGROUND OF THE INVENTION

This invention generally relates to intravascular procedures, such as percutaneous transluminal coronary angioplasty (PTCA), and particularly to the exchange of guidewires during such procedures.

In typical PTCA procedures, a dilatation catheter is advanced over a guidewire, which is slidably disposed within an inner lumen of the dilatation catheter, into the patient's coronary artery until the balloon on the distal extremity of the dilatation catheter is properly positioned across the lesion to be dilated. Once properly positioned across the lesion, the flexible, relatively inelastic balloon on the dilatation catheter is inflated to a predetermined size with radiopaque liquid at relatively high pressures (e.g., generally 4–20 atmospheres or more) to dilate the stenosed region of the diseased artery. One or more inflations of the balloon may be required to complete the dilatation of the stenosis. After the last dilatation, the balloon is deflated so that the dilatation catheter can be removed from the dilated stenosis and blood flow can resume through the dilated artery.

One significant improvement in dilatation catheters has been the introduction of rapid exchange type dilatation catheters. These catheters have a short guidewire receiving sleeve or inner lumen extending through the distal portion of the catheter which extend from a distal guidewire port in the distal end of the catheter to a proximal guidewire port spaced proximal to the proximal end of the dilatation balloon. The proximal guidewire port is usually located at least about 10 cm and usually not more than about 50 cm from the distal guidewire port. A slit is preferably provided in the catheter wall in fluid communication with the guidewire receiving inner lumen which extends from the second guidewire port, preferably to a location proximal to the proximal end of the inflatable balloon to aid in the removal of the catheter from a guidewire upon withdrawal of the catheter from the patient. The structure of the catheter allows for the rapid exchange of the catheter without the need for the use of an exchange wire or adding a guidewire extension to the proximal end of the guidewire. The design of this catheter has been widely praised by the medical profession and has met with much commercial success in the market place because of its unique design. The rapid exchange type dilatation catheters of the assignee of the present invention, Advanced Cardiovascular Systems, Inc., have had a significant impact in the market for rapid exchange type dilatation catheters. Such products include dilatation catheters sold under the trademarks ALPHA, STREAK and ELIPSE.

Rapid exchange type dilatation catheters are described and claimed in U.S. Pat. No. 5,040,548 (Yock), U.S. Pat. No. 5,061,273 (Yock), U.S. Pat. No. 5,300,085 (Yock), U.S. Pat. No. 5,350,395 (Yock), U.S. Pat. No. 4,748,982 (Horzewski et al.), U.S. Pat. No. 5,154,725 (Leopold) and U.S. Pat. No. 5,346,505 (Leopold) which are incorporated herein in their entirety by reference.

However, there is one significant inconvenience with the use of rapid exchange type dilatation catheter systems, namely, the inability to remove a guidewire already in place within a patient's vasculature during an angioplasty procedure without losing access to the vascular location. There has been no convenient way in which a replacement guidewire might be advanced through the vasculature and into the short guidewire receiving inner lumen in the distal extremity of a rapid exchange type dilatation catheter. These instances occur when there is a need to replace an in-place guidewire with another guidewire having a different structure, e.g. from a floppy-type design with a separate shaping ribbon to an intermediate or standard with a core wire which extends to the distal tip of the guidewire. The need to withdraw an in-place guidewire also occurs when the distal tip of the in-place guidewire needs to be reshaped to change the angle of attach to a branch coronary artery.

What has been needed and heretofore unavailable is a convenient means to withdraw an in-place guidewire from a rapid exchange type dilatation catheter and either replace the in-place guidewire with another guidewire or to reposition the in-place guidewire within the rapid exchange type dilatation catheter. The present invention satisfies these and other needs.

SUMMARY OF THE INVENTION

This invention is directed to a guidewire exchange device for use with rapid exchange type catheters and to the use of this device, particularly during an intravascular procedure such as angioplasty.

The guidewire exchange device of the invention generally comprises an elongated shaft with proximal and distal ends, a guidewire receiving inner lumen extending therein from the proximal end to a guidewire port in the distal end of the catheter. The catheter shaft has an elongated proximal section, a relatively short distal section and a intermediate section which is capable of transmitting push from the proximal shaft section to the distal shaft section and which is sufficiently axially flexible to allow the distal shaft section to be deflected away from the longitudinal axis of the proximal shaft section, i.e. to facilitate the articulation of the distal shaft section with respect to the proximal shaft section. This allows the proximal end of an in-place guidewire to be back loaded through the distal shaft section and out an aperture or opening provided in the flexible intermediate shaft section. The guidewire exchange device can be advanced over an in-place guidewire until the distal end of the distal shaft section of the device is seated in the proximal guidewire port of a rapid exchange type catheter. Preferably, the distal shaft section is advance well into the guidewire receiving inner lumen of the rapid exchange type catheter. In this manner, the in-place guidewire can be readily removed from the patient by pulling on the proximal extremity thereof which extends out the proximal end of a guiding catheter without loss of access to the vascular location within the patient. A replacement guidewire can then be readily advanced through the guidewire lumen in the proximal shaft section, the guidewire passageway through the intermediate shaft section, through the inner lumen of the distal shaft section and then into the guidewire lumen of the rapid exchange type dilatation catheter. At this point the guidewire exchange device may be withdrawn. However, it may be desirable to leave the guidewire exchange device connected to the rapid exchange type dilatation catheter in the event the replacement guidewire needs to be replaced.

In the embodiment of the invention wherein the distal portion of the distal tubular member of the exchange device is adapted to be inserted into and be advanced through essentially the entire length of the relatively short guidewire receiving inner lumen of the readily exchangeable catheter is particularly suitable for use with a rapid exchange type"

dilatation catheters having perfusion ports, as described in the previously discussed McInnes et al. applications incorporated herein, which allow blood to pass through the guidewire receiving inner lumen. When using rapid exchange type dilatation catheters with perfusion ports in the catheter shaft, advancement of a replacement guidewire within the guidewire receiving inner lumen sometimes results in the passage of the guidewire out one of the perfusion holes in the catheter wall rather than the guidewire port in the distal end of the catheter. When the distal extremity of the guidewire exchange device of the invention is positioned within the guidewire receiving inner lumen of the readily exchangeable catheter, the replacement guidewire is directed to the distal guidewire port through the exchange device and cannot be advanced out one of the perfusion ports.

These and other advantages of the invention will become more apparent from the following detailed description thereof, when taken in conjunction with the accompanying exemplary drawings.

BRIEF DESCRIPTION OF THE DRAWINGS

FIG. 1 is an elevational view of the guidewire exchange device of the invention.

FIG. 2 is a transverse cross-sectional view of the device shown in FIG. 1 taken along the lines 2—2.

FIG. 3 is an enlarged transverse cross-sectional view of the device shown in FIG. 1 taken along the lines 3—3.

FIG. 4 is a longitudinal view of the device shown in FIG. 2 taken along the lines 4—4 with a stiffening mandrel extending through an inner lumen of the proximal shaft section of the device.

FIG. 5 is an elevational view of the device shown in FIGS. 1–4 with an in-place guidewire extending within the distal shaft section and passing through turns of the coil interconnecting the proximal and distal shaft sections.

FIG. 6 is an elevational view, partially in section, of the guidewire exchange device shown in FIG. 1 within a guiding catheter and with the distal shaft section proximally adjacent to a proximal guidewire port of a rapid exchange type dilatation catheter.

DETAILED DESCRIPTION OF THE INVENTION

Figure 7:
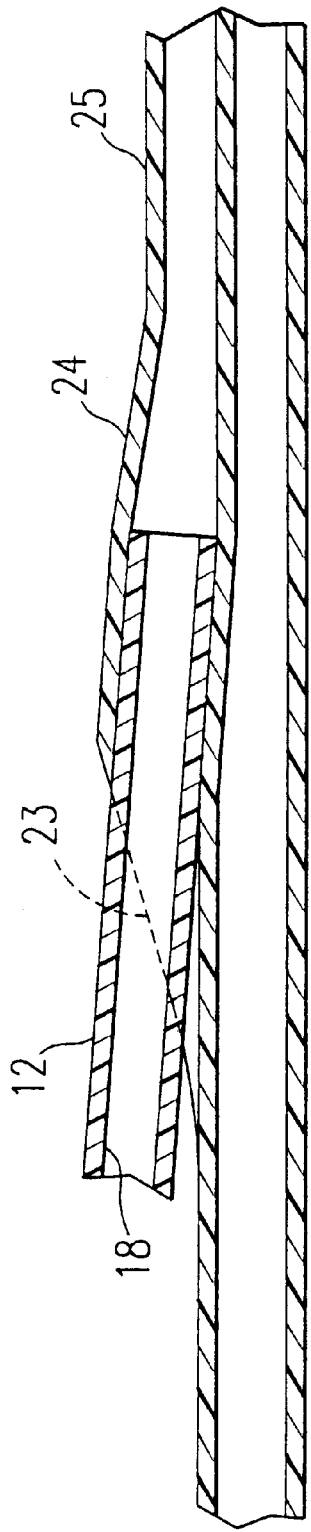
FIG. 7 is an enlarged longitudinal cross-sectional view showing the distal section of the exchanged device extending within the guidewire receiving lumen of a rapid exchange type dilatation catheter.

Reference is made to FIGS. 1–6 which depict a guidewire exchange device 10 embodying features of the invention. The exchange device 10 includes a relatively long proximal shaft section 11, a relatively short distal shaft section 12 and a flexible intermediate shaft section 13 which interconnects the distal end of the proximal shaft section to the proximal end of the distal shaft section. As shown in FIG. 2, the proximal shaft section 11 preferably has an oval shaped transverse cross-section with a first guidewire receiving lumen 14 and a second lumen 15 which receives a stiffening mandrel 16. A peel-away slit 17 is provided along a substantial length of the proximal shaft section 11 to facilitate removal of the device from a replacement guidewire at the end of the guidewire exchange procedure which will be discussed further below. The distal shaft section 12 of the exchange device 10 is relatively short and has an guidewire receiving lumen 18. The intermediate shaft section 13 is preferably a helical coil which may be formed of suitable material such as stainless steel, NITINOL or a high strength plastic material. The guidewire passageway 19 defined by the coil of the intermediate shaft section 13 extends from the proximal end of the distal section 12 to the distal end of the proximal shaft section 11 and interconnects the guidewire receiving lumen 14 of the proximal shaft section with the guidewire receiving lumen 18 in the distal shaft section. While not shown in the drawings, the proximal end of the intermediate shaft section 13 is preferably bonded by a suitable adhesive to the distal end of the proximal shaft section and the distal end of the intermediate shaft is similarly bonded to the proximal end of the distal shaft section. The proximal end of the intermediate shaft section 13 may be provided with an oval cross-sectional shape to facilitate placement onto the distal end of the oval shaped proximal shaft section 11. Aperture 20 is formed by the expanded turns of the coil.

The guidewire exchange procedure with the exchange device of the present invention is best described with respect to FIGS. 5–7. When the operating physician wishes to exchange an in-place guidewire 21 during an angioplasty or other intraluminal procedure using a rapid exchange type catheter, the proximal end of the in-place guidewire, which is located outside of the patient, is first introduced through the guidewire port 22 in the distal end of the distal shaft section 12 into the guidewire receiving lumen 18 extending in the distal shaft section and into the passageway 19 at least partially defined by the coil of the intermediate shaft section 13. The distal shaft section 12 is manually deflected so as to guide the advancing proximal end of the in-place guidewire 21 though the aperture 20 defined by adjacent turns of the coil. The proximal end of the in-place guidewire 21 is then held while the exchange device 10 is pushed from the proximal shaft section 11, which extends out of the patient, so as to advance the distal section 12 over the in-place guidewire 21 until the distal shaft section 12 of the exchange device 10 extends through the proximal guidewire port 23 of the dilatation catheter 24 and into the guidewire receiving inner lumen thereof 25, as shown in FIG. 7. The dilatation catheter 24 is preferably positioned within the patient so that the proximal guidewire port 23 thereof remains within the inner lumen 26 of the guiding catheter 27 as shown in FIG. 6. With the guidewire exchange device 10 disposed preferably well within the guidewire lumen 25 of the dilatation catheter 24, the in-place guidewire 21 may then be withdrawn from the patient by pulling on the proximal extremity of the guidewire which extends out of the patient. A replacement guidewire 28, shown in FIGS. 6 and 7, may then be advanced out of the proximal shaft section 11, through the distal shaft section 12, such as shown in FIG. 5, until the distal section of the replacement guidewire is disposed within the guidewire receiving lumen of the dilatation catheter 24. The guidewire exchange device 10 may then be withdrawn from the patient by pulling on its proximal end leaving the replacement guidewire 28 in place. The replacement guidewire 28 may be positioned within the lumen 14 of the proximal shaft section 11 before the guidewire exchange device 10 is introduced into the patient or it may be introduced into the proximal shaft section 11 after the guidewire exchange device is advanced into position within the patient.

When the guidewire exchange device 10 is withdrawn from the patient, the device is pulled off the guidewire though the peel away slit 17 provided in the proximal shaft section 11. As the proximal extremity of the replacement guidewire 28 is exposed distal to the distal end of the exchange device 10, the guidewire is manually grasped by the physician so that the device 10 can be completely removed from the guidewire. If desired the exchange device 10 may be left in the patient just in case the replacement guidewire needs to be replaced.

The proximal shaft section 11 is preferably formed from a high density polyethylene, although other conventional polymers used in forming catheter shafts may be employed such as polyvinyl chloride and co-polyesters (Hytrel). Stainless steel, NITINOL and fiber reinforced composite constructions are also suitable. The proximal shaft section 11 is about 80 to about 140 cm in length, preferably about 90 to about 110 cm. The major axis of the elliptical transverse cross-section in about 0.045 to about 0.075 inch (1.1–1.9 mm), preferably about 0.055 to about 0.065 inch (1.4–1.7mm) and the minor axis thereof is about 0.02 to about 0.04 inch (0.5–1.0 mm), preferably about 0.025 to about 0.35 inch (0.6–0.9 mm) in diameter. The guidewire receiving lumen 14 has a preferred diameter of about 0.012 to about 0.022 inch (0.310–0.6 mm) and the mandrel receiving lumen 15 has a preferred diameter of about 0.012 to about 0.022 inch. The mandrel 16 preferably has essentially the same diameter of the second lumen 15. The mandrel 16 may be formed of suitable high strength materials such as stainless steel, NITINOL and high strength polymer materials. When the proximal shaft section 11 is formed of stainless steel, NITINOL and the like the mandrel 16 may be unnecessary, in which case the dual lumen and the oval shape of the proximal shaft section also become unnecessary.

The distal shaft section 12 is preferably relatively stiff to facilitate its advancement into the guidewire port of a rapid exchange type catheter. It may be formed of polyimide, stainless steel, NITINOL or other suitable high strength materials. The distal shaft section 12 is short in comparison with the proximal shaft section 11 and is generally about 1.5 to about 4 cm, preferably about 1.5 to about 3 cm in length. The guidewire receiving lumen 18 has a diameter about 0.012 to about 0.022 inch (0.3–0.6 mm) and may be slightly smaller than the lumen 18 in the proximal shaft section 11. If the distal shaft section 12 is formed of polyimide, the wall thickness thereof may be about 0.0005 to about 0.0015 inch (0.013–0.038 mm).

The readily exchangeable dilatation catheter 24 can be exchanged for another readily exchangeable dilatation catheter over either the in-place guidewire 21 or the replacement guidewire 28.

Figure 8:
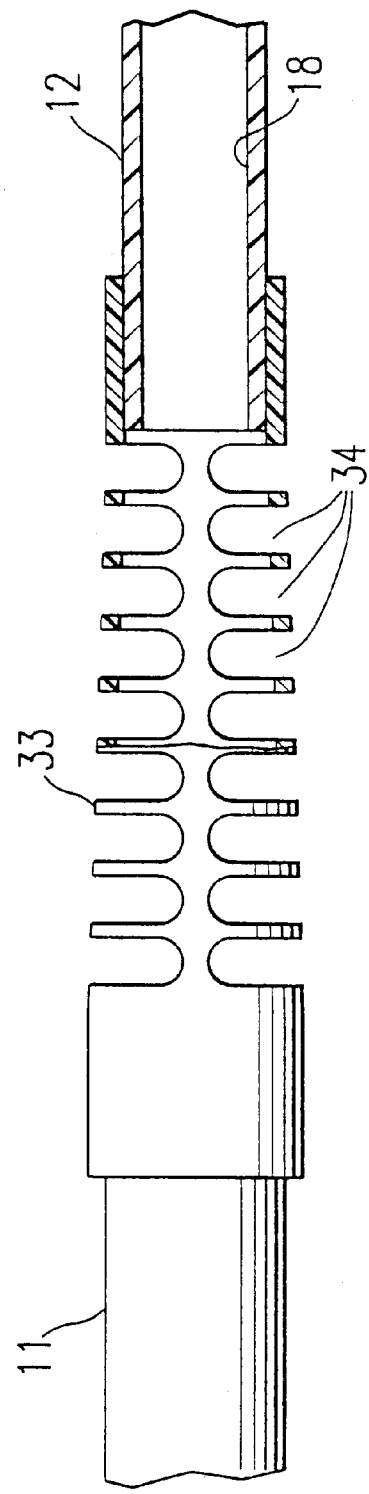
FIG. 8 is an elevational view, partially in section, of an alternative embodiment of the invention wherein the flexible intermediate shaft section of the exchange device is a tubular member with transverse slots therein.

FIG. 8 illustrates an alternative embodiment wherein the intermediate shaft section 33 is provided with a plurality of transverse slots 34 to provide the flexibility required for the articulation of the distal shaft section 12. While slots 34 are shown in this embodiment on both sides of the intermediate shaft section 33, slots may be formed on only one side to provide articulation in only one direction, if desired.

While the invention has been described herein in terms of a guidewire exchange device which facilitates guidewire replacement in a readily exchangeable dilatation catheter, those skilled in the art will recognize that the exchange device can be used with a variety of intraluminal catheters having rapid exchange features. Other modifications and improvements can be made to the invention without departing from the scope thereof.

What is claimed:

1. A guidewire exchange device having an elongated shaft comprising:

an elongated proximal shaft section with a first guidewire receiving inner lumen extending therein, an elongated slit extending longitudinally along a substantial length of the proximal shaft section, and an elongated stiffening mandrel secured to the elongated proximal shaft section, a distal shaft section with a distal end, a port in the distal end and a second guidewire receiving inner lumen extending therein and in fluid communication with the port in the distal end; and an intermediate shaft section having a guidewire passageway interconnecting the first guidewire receiving inner lumen of the proximal section and the second guidewire receiving inner lumen of the distal shaft section and an aperature in the sidewall of the intermediate shaft section for egress of a guidewire.

2. The guidewire exchange device of claim 1 wherein the length of the proximal shaft section is substantially greater than the length of the distal shaft section.

3. The guidewire exchange device of claim 1 wherein the elongated stiffening mandrel is comprised of a metal.

4. The guidewire exchange device of claim 1 wherein the elongated stiffening mandrel is comprised of a metal selected from the group consisting of NiTi and stainless steel.

5. The guidewire exchange device of claim 1 wherein the elongated stiffening mandrel has a transverse dimension of about 0.012 to about 0.022 inches.

6. The guidewire exchange device of claim 1 wherein the distal shaft section is about 1.5 to about 4 cm in length.

7. The guidewire exchange device of claim 1 wherein the distal shaft section is about 1.5 to about 3 cm in length.

\* \* \* \* \*